United States Patent [19]

Meyer et al.

[11] 4,082,763

[45] Apr. 4, 1978

[54] PROCESS FOR PRODUCING 3-HYDRAZINO-4-AMINO-5-MERCAPTO-1,2,4-TRIAZOLE

[75] Inventors: Gerhard Meyer; Anton Toth, both of Obernburg, Main, Germany

[73] Assignee: Akzona Incorporated, Asheville, N.C.

[21] Appl. No.: 593,572

[22] Filed: Jul. 7, 1975

[30] Foreign Application Priority Data

Jul. 13, 1974 Germany .............................. 2433746

[51] Int. Cl.$^2$ .......................................... C07D 249/12
[52] U.S. Cl. .............................. 260/308 R; 260/308 C
[58] Field of Search ....................... 260/308 R, 308 C

[56] References Cited

U.S. PATENT DOCUMENTS 2,726,263  12/1955  Audrieth et al. .............. 260/552 SC
3,929,877  12/1975  Toth et al. ........................ 260/308 R

OTHER PUBLICATIONS

Audrieth et al., J. Org. Chem., vol. 19, pp. 733–741 (1954).

*Primary Examiner*—Raymond V. Rush
*Attorney, Agent, or Firm*—Keil, Thompson & Shurtleff

[57] ABSTRACT

A process for the production of 3-hydrazino-4-amino-5-mercapto-1,2,4-triazole wherein hydrazinium-dithiocarbazinate is heated at moderately elevated temperature, e.g. about 50° C. to 85° C. and under reduced pressure, e.g. about 50 to 500 mm. Hg, with at least a 3× molar amount of hydrazine hydrate.

9 Claims, No Drawings

PROCESS FOR PRODUCING 3-HYDRAZINO-4-AMINO-5-MERCAPTO-1,2,4-TRIAZOLE

The compound 3-hydrazino-4-amino-5-mercapto-1,2,4-triazole was described for the first time by Stolle and Bowles in Chem. Ber. 21, p. 1101 (1908) by lengthy heating of thiocarbohydrazide with hydrazine hydrate at 120°-130° C. Dickinson and Jacobsen have repeated this synthesis by introducing for each mol of thiocarbohydrazide about 20 mols of a 99-100% hydrazine hydrate and then heating the reaction mixture for two hours on a steam bath. Yields of about 73% of theory were achieved in this manner. The authors, under these latter conditions, also obtained in addition to unreacted thiocarbohydrazide numerous other compounds which likewise contain a thiourea group capable of undergoing hydrazinolysis. In no case, however, did they obtain higher yields of 3-hydrazino-4-amino-5-mercapto-1,2,4-triazole. See Analytical Chemistry, 41, No. 10, pp. 1324–7 (1969).

As by-products to the triazole in the hydrazinolysis, some other sulfur compounds also are formed, e.g. in the heating of N,N'-dithiocarbamylhydrazine with aqueous hydrazine hydrate [Hoggarth, Journ. Chem. Soc. 1952, p. 4817], in the refluxing of benzyl-N,N'-dimethyl-dithiocarbamate or β-2,4-dichlorophenoxyethyl-N,N'-dimethyl-dithiocarbamate with excess hydrazine hydrate in ethanol [Kulka, Can. Journ. Chem., Vol. 34, p. 1093 (1956)], as well as in the heating of an aqueous solution of ethylxanthogenic acid ethyl ester with hydrazine at 50°-60° C. [Audrieth et al., Journ. Org. Chem. 19, pp 7S3–41 (1Y54)] or with 80% hydrazine hydrate [Beyer et al., Chem. Ber. 87, pp. 1401–7 (1954)]. Strube et al using the last-mentioned reaction with excess hydrazine even specify a yield of 66.6% of theory [Journ. Am. Pharm. Assoc. 48, pp. 73–5 (1959)].

According to the process in U.S. Pat. No. 3,183,241, the triazole is obtained by reacting stoichiometric amounts of dimethyltrithiocarbonate and triaminoguanidine in dimethylformamide at 115° C. However, the yield of the triazole is only 28% of theory.

It is an object of the present invention to provide a process for the production of 3-hydrazino-4-amino-5-mercapto-1,2,4-triazole which can be accomplished under moderate conditions and with excellent yields while avoiding the many disadvantages arising in the prior art.

In accordance with the invention, it has now been found that surprisingly excellent results can be achieved by producing 3-hydrazino-4-amino-5-mercapto-1,2,4-triazole by a process which comprises heating hydrazinium-dithiocarbazinate at about 50° C. to 85° C. and under reduced pressure with at least a 3X molar amount of hydrazine hydrate.

The hydrazinium-dithiocarbazinate can be produced by reaction of carbon disulfide with hydrazine hydrate according to the equation:

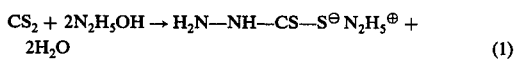

(1)

As the hydrazine hydrate, it is possible to use a commercially available technical grade, e.g. a so-called 80–85% product. Thus, it is not essential to use a completely pure hydrazine hydrate. Also, when referring herein to a water-free or anhydrous hydrazine hydrate, it should be understood that the monohydrate compound is being identified with the formula $NH_2NH_2 \cdot H_2O$ or $N_2H_5OH$. The phrase "aqueous hydrazine hydrate" refers to the fact that water has been added to the monohydrate, i.e. to form an aqueous solution thereof.

The hydrazinium-dithiocarbazinate primarily decomposes with formation of thiocarbohydrazide when heated under previously suggested process conditions, i.e. according to the following equation:

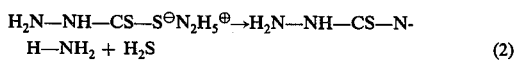

(2)

See especially prior copending application Ser. No. 524,931, filed Nov. 18, 1974, now U.S. Pat. No. 3,929,877, in which thiocarbohydrazide is produced as the desired product.

By comparison, the hydrazinium-dithiocarbazinate is reacted in accordance with the present invention so as to primarily yield 3-hydrazino-4-amino-5-mercapto-1,2,4-triazole as the desired product, and under preferred or optimum process conditions, one can achieve practically a quantitative conversion into the desired triazole. It is conceivable that the thiocarbohydrazide formed in the reaction according to equation (2) reacts further with hydrazinium-dithiocarbazinate to form an intermediate compound, hydrazine dithiocarboxylic acid hydrazide, in accordance with the equation:

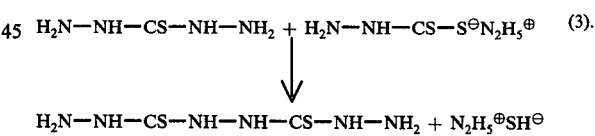

This intermediate compound is then cyclized from its tautomeric thiol form while splitting off hydrogen sulfide to produce the 3-hydrazino-4-amino-5-mercapto-1,2,4-triazole according to the following equation (4):

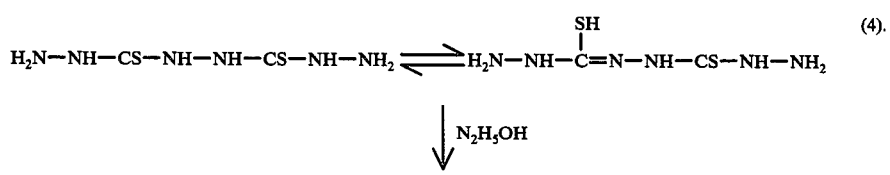

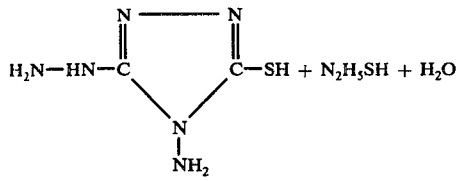

It is possible for purposes of the fresent invention to ordance with the equation:

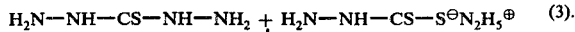
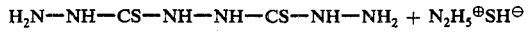

$H_2N-NH-CS-NH-NH-CS-NH-NH_2 + N_2H_5^{\oplus}SH^{\ominus}$ use either aqueous hydrazine hydrate or the water-free hydrazine hydrate, but for economical reasons it is desirable to use this compound in an aqueous solution, i.e. as the aqueous hydrazine hydrate. The aqueous hydrazine hydrate is preferably one having a water content of up to about 50% by weight and especially up to about 30% by weight. Within this range, the formation of the triazole is substantially independent of the concentration of the water in the reaction mixture. However, even more dilute aqueous solutions of the hydrazine hydrate may be used in the process of the invention.

The hydrazine hydrate, calculated as the water-free monohydrate must be used in at least a 3-fold molar amount, i.e. three times or 3X of the molar amount of the hydrazinium-dithiocarbazinate used in the reaction. With smaller molar amounts of hydrazine hydrate, the reaction proceeds primarily toward the formation of thiocarbohydrazide. As the amount of the hydrazine hydrate is increased from about said 3X molar amount up to about a 6X molar amount, there is also an increase in the yield of the desired triazole. However, at a molar ratio of hydrazine hydrate:hydrazinium-dithiocarbazinate of approximately 5:1, the triazole yield already amounts to more than 99% of theory. A further increase of the proportion of the hydrazine hydrate provides no advantage and consequently will not ordinarily be considered as having any purpose in producing the triazole product. For these reasons, the present invention is preferably restricted to the use of about 4 to 6 mols, especially about 5 mols, of hydrazine hydrate for each mol of hydrazinium-dithiocarbazinate.

The reaction of the hydrazinium-dithiocarbazinate proceeds advantageously at temperatures of about 50° C. to 85° C. Reaction temperatures above 85° C. should be avoided because under these conditions the reaction tends to proceed too vigorously to be properly controlled and there even exists a serious danger that the reaction mixture will explode. At temperatures below 50° C., a formation of triazole does begin to take place but the reaction speed is correspondingly slight. Accordingly, the process of the invention is preferably carried out in the range of about 50° C. to 80° C. and especially from about 70° C. to 77° C. In any large scale or technical synthesis of the triazole, the reaction temperature preferably should not exceed 77° C. in order to avoid losses due to the thermal decomposition of the hydrazine hydrate.

It is also essential to carry out the process of the invention under a reduced pressure, i.e. at pressures below atmospheric pressure, using any suitable means to provide a partial vacuum. This reduced pressure permits the hydrogen sulfide formed in the decomposition of the hydrazinium-dithiocarbazinate according to equation (2) above to be separated off from the liquid reaction phase during the course of the reaction. By mechanically agitating or stirring the liquid reaction mixture, using conventional equipment for this purpose, this degassing or removal of hydrogen sulfide can be accelerated. It is preferable to work at pressures (absolute) of about 50 to 500 mm. Hg, especially from about 200 to 250 mm. Hg.

The following procedure can be followed in carrying out the process of the invention. At first, the hydrazinium-dithiocarbazinate can be admixed with the water-free or aqueous hydrazine hydrate in a reaction vessel which is then evacuated to the desired reduced pressure and the reaction mixture heated. During this initial procedure, the hydrazine thiocarbazinate goes gradually into solution, and the reaction begins after approximately 15-20 minutes with a strong generation of hydrogen sulfide. The 3-hydrazino-4-amino-5-mercapto-1,2,4-triazole partly crystallizes out of the liquid phase even during the course of the reaction.

After the reaction is completed and the reaction mixture is cooled, most of the reaction product can be separated by filtration. The mother liquor contains, in addition to some thiocarbohydrazide as a by-product, a small proportion of the 3-hydrazino-4-amino-5-mercapto-1,2,4-triazole still dissolved therein. This additional thiazole product can be recovered by concentrating the mother liquor, e.g. by evaporation. Since the concentrated mother liquor has a tendency to explode when heated, a single stage, strong concentration is not possible. Instead, one should take the precaution of concentrating and filtering off a triazole fraction several times in succession. The mother liquor can then be recycled when operating a continuous or at least semi-continuous process, or this mother liquor may also be reused in successive batch processes.

It is not absolutely necessary to proceed from hydrazinium-dithiocarbazinate as an initial material. Instead, it is also possible in a further development of the process according to the invention to first prepare a reaction mixture obtained by the reaction of carbon disulfide and excess hydrazine hydrate. The same process conditions are followed in this embodiment of the invention as given for the decomposition of the hydrazinium-dithiocarbazinate. Preferably, however, the carbon disulfide is initially brought into reaction with a 6X to 8X molar amount of hydrazine hydrate, calculated as the water-free monohydrate, at a temperature of about 0° to 25° C., and the reaction mixture obtained in this manner is then further reacted in the above-noted manner at about 50°-85° C., preferably 50°-80° C. and especially 70°-77° C., while continuously separating or degassing the hydrogen sulfide arising in the reaction. It can be assumed that the hydrazinium-dithiocarbazinate is formed as the essential intermediate when beginning with excess hydrazine hydrate and carbon disulfide.

However, the reactions can proceed concurrently in a single stage so that one need not separate or recover the intermediate reactant. Again, the excess hydrazine hydrate can be recovered and recycled so as to be substantially completely used in repeated or continuous processes.

The process of the invention has important advantages when compared to the known processes of producing 3-hydrazino-4-amino-5-mercapto-1,2,4-triazole. In all of the known processes, the yields are substantially smaller. Beyond this, the process of the invention offers the possibility of synthesizing 3-hydrazino-4-amino-5-mercapto-1,2,4-triazole in a direct manner from hydrazine hydrate and carbon disulfide, whereby one can carry out a so-called "single pot" or one stage reaction in a single vessel or single stage.

3-Hydrazino-4-amino-5-mercapto-1,2,4-triazole is a known compound useful in analytical chemistry as a specific reagent for aldehydes (see Dickinson et al, supra). It is also valuable for use in the production of bactericides.

The invention is further illustrated but not limited by the following examples.

EXAMPLES 1 – 5

In a reaction flask equipped with a reflux condenser, there were brought together for reaction 17.5 grams (0.125 mol) of hydrazinium-dithiocarbazinate and 13.5 grams (0.75 mol) of water with water-free hydrazine hydrate. The amount of hydrazine hydrate was the only parameter changed in each example. The reaction temperature was 75° C., the pressure was 250 mm. Hg and the reaction time amounted to about 6 hours.

After 15–20 minutes, the hydrazinium-dithiocarbazinate went completely into solution and it was possible to observe the vigorous generation of hydrogen sulfide gas. This evolved gas was continuously withdrawn by means of a vacuum pump so as to maintain an approximately constant reduced pressure of 250 mm. Hg. After about 2.5 hours, the 3-hydrazino-4-amino-5-mercapto-1,2,4-triazole began to deposit as a crystalline precipitate. After completion of the reaction and cooling, this precipitate was filtered by suction to recover the bulk of the product. The mother liquor was then concentrated to about half the original amount, whereby a further fraction of the triazole product could be separated by filtration. This concentration of the mother liquor was repeated so that altogether three separate fractions of triazole were recovered. All of the precipitated triazole was joined together, washed several times with hot water and then dried.

The melting of the triazole in all cases was 227° C., and this product was consequently almost analytically pure.

In Table 1, the particular amounts of hydrazine hydrate, the molar ratios in the initial reaction mixture and the resulting yields of 3-hydrazino-4-amino-5-mercapto-1,2,4-triazole are given for each of the first five examples. The abbreviation "HDC" is used to identify hydrazinium-dithiocarbazinate. It will be noted that the yield drops to a very low value when using less than a 3X molar amount of hydrazine hydrate as shown by the first (comparative) example.

TABLE 1

| Ex. No. | $N_2H_5OH$ (grams) | Molar ratio $HDC:N_2H_5OH:H_2O$ | Triazole Yield (% of Theory) |
|---|---|---|---|
| 1 (comparison) | 12.50 | 1 : 2 : 6 | 3.3 |
| 2 | 18.75 | 1 : 3 : 6 | 82.1 |
| 3 | 25.00 | 1 : 4 : 6 | 87.7 |
| 4 | 31.25 | 1 : 5 : 6 | 99.2 |
| 5 | 37.50 | 1 : 6 : 6 | 99.2 |

EXAMPLES 6 – 9

In the same manner as described in the first five examples, 17.5 grams (0.125 mol) of hydrazinium-dithiocarbazinate (HDC) are reacted in each case with 31.25 grams (0.625 mol) of hhydrazine hydrate ($N_2H_5OH$) either as the water-free monohydrate or with various amounts of water. Table 2 summarizes the results of this series of tests, and it will be noted that the presence or absence of water has practically no effect on the yields of the thiazole. This product in each case was quite pure, exhibiting a melting point of 227° C,

TABLE 2

| Ex. No. | Water (grams) | Molar ratio $HDC : N_2H_5OH : H_2O$ | Triazole Yield % of Theory |
|---|---|---|---|
| 6 | — | 1 : 5 : 0 | 99.2 |
| 7 | 4.5 | 1 : 5 : 2 | 99.0 |
| 8 | 9.0 | 1 : 5 : 4 | 99.5 |
| 9 | 13.5 | 1 : 5 : 6 | 99.3 |

EXAMPLE 10

In this example, the process is carried out in accordance with the invention but proceeding directly from carbon disulfide and excess hydrazine hydrate in a "single pot" reaction.

Using the same flask as described in the first five examples, 9.5 grams (0.125 mol) of carbon disulfide was introduced and admixed with stirring and cooling into 43.75 grams (0.875 mol) of hydrazine hydrate and 9 grams (0.5 mol) of water. This represents an initial molar ratio of $CS_2 : N_2H_5OH : H_2O$ of 1 : 7 : 4; but because 2 mols of $N_2H_5OH$ are used for each mol of carbon disulfide to form hydrazinium-dithiocarbazinate (HDC), the initial reaction mixture is essentially equivalent to the preferred molar ratio $HDC : N_2H_5OH : H_2O$ of 1 : 5 : 6 in accordance with equation (1) above.

The temperature of the initial reaction mixture was maintained at 0° C. by cooling until completion of the first reaction between carbon disulfide and hydrazine hydrate. The resulting reaction mixture containing the still unreacted hydrazine hydrate and water together with the intermediate hydrazinium-dithiocarbazinate was then placed under reflux in the same flask, using a vacuum of 250 mm. Hg and slowly heating the mixture up to 75° C. The further reaction and working up of the thiazole reaction product then proceeded as in the first five examples. The yield of 3-hydrazino-4-amino-5-mercapto-1,2,4-triazole amounted to 99.4% of theory, m. p. = 227° C.

The invention is hereby claimed as follows:

1. A process for the selective production of 3-hydrazino-4-amino-5-mercapto-1,2,4-triazole which comprises heating hydrazinium-dithiocarbazinate with 4 to 6 mols of hydrazine hydrate for each mol of hydrazinium-dithiocarbazinate at about 50° C. to 85° C. and under a sufficiently reduced pressure to separate off byproduct hydrogen sulfide, and recovering said triazole as the primary reaction product from the reaction mixture in a yield of about 87.7 to 99.5%.

2. A process as claimed in claim 1 wherein an aqueous hydrazine hydrate is used with a water content of up to about 50% by weight.

3. A process as claimed in claim 2 wherein said water content is up to about 30% by weight.

4. A process as claimed in claim 1 wherein approximately 5 mols of hydrazine hydrate are used for each mol of hydrazinium-dithiocarbazinate.

5. A process as claimed in claim 1 wherein the reaction is carried out at a pressure of about 50 to 500 mm. Hg.

6. A process as claimed in claim 4 wherein the reaction is carried out at a pressure of about 200 to 250 mm. Hg.

7. A process as claimed in claim 1 wherein the reaction temperature is about 70° C. to 77° C.

8. A process as claimed in claim 1 wherein the hydrazinium-dithiocarbazinate is prepared as the reaction mixture of carbon disulfide with an excess of the hydrazine hydrate.

9. A process as claimed in claim 1 carried out with about 5 to 6 mols of hydrazine hydrate for each mol of hydrazinium-dithiocarbazinate to provide a yield of said triazole of about 99.0 to 99.5%.

* * * * *